(12) United States Patent
Voudouris et al.

(10) Patent No.: US 6,368,105 B1
(45) Date of Patent: Apr. 9, 2002

(54) ORTHODONTIC BRACKET AND ITS TOOL

(76) Inventors: John C. Voudouris, 16, Doan Road, Toronto, Ontario (CA); Masaaki Orikasa, c/o Tomy Incorporated, 818, Shinmachi, Ohkuma-machi, Futaba-gun, Fukushima 979-1305 (JP)

( * ) Notice: Subject to any disclaimer, the term of this patent is extended or adjusted under 35 U.S.C. 154(b) by 0 days.

(21) Appl. No.: 09/684,749

(22) Filed: Oct. 6, 2000

(30) Foreign Application Priority Data

| Oct. 8, 1999 | (JP) | ............................................ 11-288785 |
| Apr. 24, 2000 | (JP) | ....................................... 2000-010695 |
| Apr. 24, 2000 | (JP) | ....................................... 2000-010696 |
| Apr. 24, 2000 | (JP) | ....................................... 2000-010697 |

(51) Int. Cl.[7] ............................................... A61C 3/00
(52) U.S. Cl. ....................................................... 433/11
(58) Field of Search ............................. 433/10, 11, 13, 433/14

(56) References Cited

U.S. PATENT DOCUMENTS

| 4,492,573 A | * | 1/1985 | Hanson | ........................ 433/11 |
| 5,906,486 A | * | 5/1999 | Hanson | ........................ 433/11 |
| 5,913,680 A | * | 6/1999 | Voudouris | ..................... 433/11 |
| 6,071,119 A | * | 6/2000 | Christoff et al. | ............... 433/13 |
| 6,193,508 B1 | * | 2/2001 | Georgakis | ..................... 433/11 |

* cited by examiner

Primary Examiner—Cary E. O'Connor
(74) Attorney, Agent, or Firm—Kenyon & Kenyon

(57) ABSTRACT

An orthodontic bracket has a locking member, one side of which is formed as a base side portion located on a base side and extending along the base, and the other side of which is formed as a counter base side portion having substantially the same width as the length of an arch wire slot 5 and extending on an upper side of the slot. The locking member is formed of an elastic member in which a notched portion is provided substantially in a center of the base side portion. Further, a bracket body has a closing stop groove formed at an open edge portion of the arch wire slot so as to stop a tip of the locking member in a slot closed position as well as an open stop concavity formed at an edge portion thereof located away from the stop groove so as to stop the tip of the locking member in a slot open position. A rib is formed in a longitudinally central portion of the stop groove in such a manner as to project so as to bury the stop groove in correspondence with the notched portion.

20 Claims, 14 Drawing Sheets

ORTHODONTIC BRACKET AND ITS TOOL

BACKGROUND OF THE INVENTION

1. Field of the Invention

The present invention relates to an orthodontic bracket, and more particularly to an orthodontic bracket having a shiftable locking member so as to open or close an arch wire slot in a bracket body as well as a tool for an orthodontic bracket.

2. Description of the Related Art

As is known, orthodontic treatment is effected by fixing small appliances called orthodontic brackets to a patient's teeth. Namely, the orthodontic brackets are most commonly used by being fixed to the patient's teeth in an appropriate manner so as to correct the misaligned teeth by applying an external force thereto through an arch wire extending between the fixed orthodontic brackets.

As to the structure of these orthodontic brackets, they are constructed of a body having small slots and are adhered directly on the labial or lingual sides of the teeth or welded to such as metal bands attached to the teeth by cementing or by some other method.

As the form of use of the orthodontic bracket constructed as described above, an elastic arch wire, which is curved so as to conform to a dental arch, is placed in a slot in the bracket, and the tooth can be shifted over time by the restoring force of the elastic arch wire so that the teeth become well aligned.

Namely, with the orthodontic bracket, a force can be applied to the tooth in a desired direction (in the direction in which the tooth is shifted, rotated, or tilted) by the three-dimensional inclination of the slot formed in the bracket body or by the desired bending of the arch wire.

The conventional orthodontic bracket has tie wings, and a ligature wire or an elastomeric ligature ring is hooked on the tie wings so as to positively hold the arch wire to prevent the arch wire from coming out of the slot in the bracket. The dentition that should be treated is of malocclusion, in which the arch wires are greatly deformed when engaged. Orthodontic treatment is done by transmitting the restoring force of the arch wires through brackets to the tooth roots. Generally, in an early period of the treatment, a thin soft round wire is used, and an operation is required to loosen the ligature wire after ligating it such that the round wire freely slides within the slot (on a nonfrictional basis). In addition, the frictional force cannot be eliminated with the elastomeric ligature ring.

As treatment progresses, a thicker wire, a square wire, and a more highly rigid wire come to be used. When the shifting treatment is nearly completed, they are held for a while to prevent relapsing. At this time, there are cases where the tooth is strongly fastened by a ligature wire so that it practically does not shift.

In the orthodontic treatment as described above, different arch wires of many varieties are used in succession during the course of the treatment. During patient visits to the clinic, it is necessary to remove the ligature wire and adjust the bend of the arch wire or replace it. This operation requires much chair time and imparts discomfort to the patients.

In addition, an end of the ligature wire which has been cut after ligation is accommodated so as to be bent and thrust into a groove under the tie wing. Such modes of attachment lead to problems of food residues tending to adhere. As a result, comparatively large number of measures had to be taken in order to maintain good hygienic conditions inside the teeth. In addition, there are cases where the ligature wire causes the trouble of imparting stimuli to the soft tissue of the patient's tongue or cheek as its bent end becomes exposed from below the tie wing. If this ligature wire is cut and reshifted, the patient may swallow the dislocated ligature wire, or the treatment may make no progress. Further, in recent years serious concern has been expressed over various infectious diseases which occur due to bleeding caused by the piercing of the doctor's fingers by the ligature wire.

The various problems due to the use of such a ligature wire can be overcome to some extent by using a lock-type orthodontic bracket. Namely, this lock-type orthodontic bracket has the structure which does not require the tie wire for ligation, and has a locking member incorporated in the bracket and capable of shifting for opening or closing the slot in the bracket. As the locking members, there are, for example, rotating-type and sliding-type locking members. Since the locking members are capable of shifting, the retention of the arch wire in the slot or disengagement of the arch wire from the slot can be effected very easily. In addition, the structure is free of a bent portion of the ligature wire and is therefore trim, it is easy to avoid such as the sticking of food and its residue.

As shown in FIG. 13, with the orthodontic bracket having the aforementioned sliding-type locking member, an arch wire 50 in an arch wire slot 85 provided in a bracket body 82 is locked in the slot by a tip portion of a locking member 120 mounted on the bracket body 82. As for the tip portion of the locking member 120, its shift in the loosening direction is restricted by a stop groove 86 continuing to the slot 85, for example. Normally, the arch wire 50 in the slot 85 is located on the bottom side of the slot, as shown in FIG. 13. However, when an unexpected large external force is applied to the arch wire 50, the arch wire 50 can enter the stop groove 86 and become caught therein, as shown in FIG. 14.

In such a state, the arch wire 50 fails to shift smoothly inside the slot, and a hindrance is caused to the orthodontic treatment. To avoid such a state, it is conceivable to decrease the width W of the stop groove 86, but if that width W is decreased, the function of the locking member 120 (the function of pressing down the wires ranging from the narrow round wire to the full-size square wire within the range of the elasticity) declines, so that it is not desirable to do so.

In addition, there has been a problem in that when an unexpected large external force is applied to the arch wire 50, a tip portion 121 of the locking member 120 becomes twisted as the arch wire 50 is twisted, thereby rendering the wire retention unstable. In the structure disclosed in U.S. Pat. No. 5,906,486, an arrangement is shown in which the position of the tip portion of the locking member is restricted in such a manner as to close both ends of the stop groove. In such a structure, however, since the arrangement is provided so as to close both ends of the stop groove, the width of the tip portion of the locking member must be inevitably made smaller than the length of the slot. Accordingly, there has been a drawback in that the tip portion of the locking member has insufficient rotation control since its length for holding the arch wire is short.

SUMMARY OF THE INVENTION

The invention has been made to overcome the above-described problems, and its object is to provide an orthodontic bracket having a locking member which makes it possible to avoid the situation of the arch wire becoming coming out the slot and entering the stop groove, and which makes the retention of the arch wire more reliable and excels in the operating efficiency. In the orthodontic brackets of rhomboid-type and torque-in-base type orthodontic brackets, the object is to provide an orthodontic bracket excelling in the handling efficiency. Another object of the invention is to provide a tool excelling in the efficiency in handling the locking member.

In accordance with the invention, there is provided an orthodontic bracket including a base secured to a tooth surface, a bracket body extending in a substantially perpendicular direction from the base, an arch wire slot which extends in a mesiodistal direction substantially in a center of the bracket body and is open in the front, and a locking member capable of opening or closing the arch wire slot, wherein the locking member is structured in a substantially U-shaped cross-sectional configuration, one side thereof being formed as a base side portion located on a base side and extending along the base, another side thereof being formed as a counter base side portion having substantially the same width as the length of the arch wire slot and extending on an upper side of the slot, the locking member being formed of an elastic member in which a notched portion is provided substantially in a center of the counter base side portion, and that the bracket body has a closing stop groove formed at an open edge portion of the arch wire slot so as to stop a tip of the locking member in a slot closed position as well as an open stop concavity formed at an edge portion thereof located away from the stop groove so as to stop the tip of the locking member in a slot open position, a rib being formed in a longitudinally central portion of the stop groove in such a manner as to project so as to bury the stop groove in correspondence with the notched portion. Consequently, the above object can be attained.

The orthodontic bracket in accordance with the invention preferably has the following features.

The bracket body is a twin bracket having a central groove sandwiched between mesial tie wings and distal tie wings, and the rib is formed over an entire width of the central groove and is formed in such a manner as to be connected to the mesial tie wing and the distal tie wing.

The bracket body is a single bracket having a tie wing.

The bracket body is a lingual bracket which is mounted on a lingual side of a tooth.

A recessed portion is formed in an upper end surface of the rib.

An engaging end portion formed by a recess or a notch is formed at a rear end portion of the base side portion of the locking member.

The bracket body has an opening extending therethrough along the mesiodistal direction.

The bracket body has a projection provided on a side surface of the tie wing where an edge portion of the locking member slides, the projection being capable of abutting against the edge portion, the projection being arranged to be located on an outer side of the edge portion when the slot is closed by the locking member.

The bracket body is provided with a hook rising and jetting out in the mesiodistal direction of the tie wing of the bracket body.

The locking member is formed of a single plate material, and is structured such that a portion of the base side portion located close to the base with a substantially longitudinally central portion as a boundary is set at an angle of inclination conforming to the angulation of the bracket, while the counter base side portion on an opposite side away from the side close to the base is set at an angle of inclination which is obtained by correcting an angle corresponding to a bent portion for pressing the arch wire in addition to the angle of inclination of the bracket angulation, a curved portion connecting the base side portion and the counter base side portion forming a portion of a sine curve.

The bracket body has a rhomboid-type shape, and wherein mesial and distal edge portions of the counter base side portion of the locking member and mesial and distal edge portions of the base side portion, in a top view of the bracket, are formed in parallel along mesial and distal ends of the tie wing of the bracket, and edge portions of the counter base portion extending along the mesiodistal direction are formed to be parallel to the arch wire slot.

The bracket body has a non-rhomboid-type shape and is of a cut-angulation- type in which, in a plan view of the bracket body, the arch wire slot is inclined with respect to a straight line of the edge portion of the bracket body, and edge portions of the counter base side portion of the locking member extending in the mesiodistal direction are formed to be parallel to the arch wire slot.

The locking member is formed of a superelastic member.

The locking member is formed of a beta titanium alloy.

The locking member is formed of a cobalt-nickel-base alloy (Co—Ni-base alloy) containing chromium (Cr) and molybdenum (Mo).

The locking member is formed of a work-hardening nickel-titanium (Ni—Ti) alloy.

The bracket body has a torque-in-base structure, and the base side portion of the locking member is formed so as to be located in parallel to the base inclined in correspondence with torque.

The base side portion of the locking member is arranged to slide over the base.

A tool for an orthodontic bracket in accordance with the invention is characterized by comprising: a fulcrum portion engageable with a portion of the bracket body and an acting portion engageable with a rear end portion of the base side portion, wherein the locking member is operated to slide by using the portion of the bracket body as a fulcrum and an engaging end portion of the rear end portion as a point of application. Consequently, it is possible to attain the above object.

In the tool for an orthodontic bracket in accordance with the invention, the fulcrum portion is arranged to be engageable with a recessed portion in an upper end surface of the rib.

In accordance with the orthodontic bracket pertaining to the invention, the locking member is structured in a substantially U-shaped cross-sectional configuration, one side thereof being formed as the base side portion located on the base side and extending along the base, another side thereof being formed as the counter base side portion having substantially the same width as the length of the arch wire slot and extending on the upper side of the slot, the locking member being formed of an elastic member in which the notched portion is provided substantially in the center of the counter base side portion. The bracket body has the closing stop groove formed at an open edge portion of the arch wire slot so as to stop a tip of the locking member in a slot closed position as well as the open stop concavity formed at an edge portion thereof located away from the stop groove so as to stop the tip of the locking member in a slot open position.

By virtue of this arrangement, the locking member is capable of sliding on the bracket body so as to open or close the arch wire slot.

In addition, since the rib is formed in a longitudinally central portion of the stop groove in such a manner as to project so as to bury the stop groove in correspondence with the notched portion of the locking member, it is possible to avoid a situation in which the arch wire is disengaged from the slot and enters the stop groove. Further, since the notched portion of the locking member is correspondingly provided for the rib in the stop groove so as to be fitted to it, the shift and twisting of the tip portion of the locking member in the longitudinal direction of the slot can be effectively suppressed. Namely, with respect to the shift and twisting of the tip portion of the locking member in the longitudinal direction of the slot, such shift can be suppressed by the rib provided in a central region of the stop groove. Moreover, the distance for holding in the mesiodistal direction of the tip of the locking member can be made large without being restricted by the structure of the bracket body.

In addition, in the above-described orthodontic bracket in accordance with the invention, according to the arrangement in which the bracket body is a twin bracket having a central groove sandwiched between mesial tie wings and distal tie wings, and the rib is formed over the entire width of the central groove and is formed in such a manner as to be connected to the mesial tie wing and the distal tie wing, the bracket body can be reinforced by this rib.

In addition, in the above-described orthodontic bracket in accordance with the invention, if the bracket body is a single bracket having tie wings, it is possible to provide an orthodontic bracket which has a locking member and can be used for a rotated tooth or lower jaw anterior teeth having a narrow tooth width and which excels in mountability and operating efficiency.

In addition, in the above-described orthodontic bracket in accordance with the invention, if the bracket body is a lingual bracket which is mounted on a lingual side of a tooth, it is possible to provide an orthodontic bracket which has a locking member and can be used for the lingual side of the tooth for which ligation with a ligature wire is difficult and which excels in mountability and operating efficiency.

In addition, in the above-described orthodontic bracket in accordance with the invention, according to the arrangement in which a recessed portion is formed in an upper end surface of the rib, it is possible to insert a tool or the like into the recessed portion, and the recessed portion can be used at the time when the bracket body or the locking member is operated. Further, in a case where the recessed portion has, for instance, a triangular shape, it is effective for the doctor to discriminate the upper and lower sides in the axial direction of the tooth.

In addition, in the above-described orthodontic bracket in accordance with the invention, since an engaging end portion formed by a recess or a notch is formed at a rear end portion of the base side portion, the tool can be engaged in this notch or the recessed portion, and the doctor is able to easily release the locking member by operating the tool with his or her finger without directly viewing this engaging end portion.

In addition, in the above-described orthodontic bracket in accordance with the invention, since the bracket body has an opening extending therethrough along the mesiodistal direction, by making use of this opening, treatment can be effectively advanced by attaching an appropriate means for fixing the locking member, by retracting anterior teeth portion by passing an auxiliary wire therethrough, or by using an auxiliary means such as an uprighting spring, a rotation spring, or the like.

In addition, in the above-described orthodontic bracket in accordance with the invention, an arrangement is provided such that the bracket body has a projection provided on a side surface of the tie wing where an edge portion of the locking member slides, the projection being capable of abutting against the edge portion, the projection being arranged to be located on an outer side of the edge portion when the slot is closed by the locking member. Accordingly, when an unexpected external force has been applied in the oral cavity, this projection holds down a portion of the locking member (a curved portion of the locking member), so that an unintentional release of the locking member can be avoided. In addition, when an attempt is made to manipulate the U-shaped curved portion of the locking member by pressing it so as to close the slot, the clicking pressure can be felt by the finger when this projection is ridden over, so that it is possible to confirm the closure of the slot.

In the above-described orthodontic bracket in accordance with the invention, since the bracket body is provided with a hook rising and jetting out in the mesiodistal direction of the tie wing of the bracket body, when the tool is engaged with the bracket body, since the hook juts out so as to escape laterally from the bracket body, no hindrance is caused to the operating efficiency.

In the above-described orthodontic bracket in accordance with the invention, according to the arrangement in which the locking member is formed of a single plate material, the locking member can be fabricated very easily by such as blanking a plate material. In addition, the arrangement provided is such that a portion of the base side portion located close to the base by using as a boundary a substantially longitudinally central portion of the portion (leg) extending toward the base side portion in the locking member is set at an angle of inclination conforming to the angulation of the bracket, while the counter base side portion on an opposite side away from the side close to the base is set at an angle of inclination which is obtained by correcting an angle corresponding to a bent portion for pressing the arch wire in addition to the angle of inclination of the bracket angulation, a curved portion connecting the base side portion and the counter base side portion forming a portion of a sine curve. Accordingly, in a top view of the locking member, the left and right edge portions of the counter base side portion can be formed to be seen as straight lines. Hence, in the case where the shape of the bracket body is of the rhomboid type, the line of each edge portion of the counter base side portion can be utilized in the alignment of the bracket.

In the above-described orthodontic bracket in accordance with the invention, the arrangement provided is such that the bracket body has a rhomboid-type shape, and wherein mesial and distal edge portions of the counter base side portion of the locking member and mesial and distal edge portions of the base side portion, in a top view of the bracket, are formed in parallel along mesial and distal ends of the tie wing of the bracket, and occlusal edge portions (edge portions close to the base side portion) of the counter base portion and a gingival side edge portion of the notched portion (an edge portion at an innermost portion of the notch) are formed to be parallel to the arch wire slot. Accordingly, in a top view of the bracket, these edge portions are parallel to the respective sides of a parallelogram of the bracket, so that the respective edge portions of the locking member in the mesiodistal direction and in the axial direction of the tooth can be utilized in the alignment of the bracket.

In the above-described orthodontic bracket in accordance with the invention, the arrangement provided is such that the bracket body is of a cut angulation type in which the arch wire slot is inclined with respect to a contour line of a square (non-rhomboid) bracket, and edge portions (tip edge portions, occlusal-side edge portions, and the gingival-side edge portion in the notched portion) of the counter base side portion of the locking member extending in the mesiodistal direction are formed to be parallel to the arch wire slot. Accordingly, in the orthodontic bracket of the cut angulation type, the respective edge portions of the locking member can be utilized in the alignment and orientation.

In the orthodontic bracket in accordance with the invention, since the locking member is formed of a super-elastic member, i.e., a member having a state in which even if the amount of deformation has increased more than a specific amount, the change in load does not increase and is maintained at a substantially fixed level. Therefore, even if the locking member has undergone relatively large deformation, there is no major change in the load, and it is possible to maintain favorable operating efficiency in the moderate holding down of the arch wire and in the treatment operation.

In addition, in the orthodontic bracket in accordance with the invention, if the locking member is formed of a beta • titanium alloy, since it is possible to enlarge the pressing force (load) relative to the amount of deformation, the slot can be sealed reliably and the arch wire can be pressed positively.

Further, in the orthodontic bracket in accordance with the invention, if the locking member is formed of a cobalt-nickel-base alloy (Co—Ni-base alloy) containing chromium (Cr) and molybdenum (Mo), e.g., Elgiloy (trade name) manufactured by Elgin Inc. of the United States or SPRON (trade name) of SII Micro Parts Inc., since relatively large amounts of chromium and molybdenum are contained, such an alloy is able to exhibit high fatigue resistance and corrosion resistance although it has an excellent spring characteristic.

In addition, in the orthodontic bracket in accordance with the invention, if the locking member is formed of a work-hardening nickel-titanium (Ni—Ti) alloy, since the elastic limit in the case of this alloy is also high, the slot can be sealed reliably and the arch wire can be pressed positively.

In addition, in the orthodontic bracket in accordance with the invention, if the bracket body has a torque-in-base structure, the pressing direction of the counter base side portion of the locking member with respect to the arch wire can be substantially set in a fixed manner. Accordingly, since the arch wire can be maintained in the slot with the orientation and magnitude of a stable pressing force, an effect of accurate treatment can be expected. Namely, even in a case where a plurality of bracket bodies of different forms are used, since the relationship between the arch wire and the locking member can be fixed in any case, it is easy to estimate the treatment effect, and a positive effect of treatment can be expected. In addition, since the arrangement provided is such that the base side portion of the locking member is formed so as to be located in parallel to the base inclined in correspondence with torque, and is located close to the bonding base in any case of the torque, the tip portion of the base side portion is not located so as to block the space below the tie wings, so that the amount of food residue stuck can be reduced.

In addition, since the base side portion of the locking member is arranged to slide over the base, the base side portion at any position is held by the base. For example, even in a case where the operation of strongly pressing its rear end by a tool is effected, the base side portion is able to open stably without becoming deformed.

The tool for an orthodontic bracket in accordance with the invention is characterized by comprising: a fulcrum portion engageable with a portion of the bracket body and an acting portion engageable with a rear end portion of the base side portion, wherein the portion of the bracket body is used as a fulcrum and an engaging end portion of the rear end portion is used as a point of application. Hence, when, for example, the operation of opening the locking member (the operation of opening the slot) is effected, it is possible to apply a force for sliding the locking member while holding down the bracket body with one tool, thereby making it possible to effect the sliding operation smoothly.

In addition, if the tool for an orthodontic bracket is arranged such that the fulcrum portion is arranged to be engageable with a recessed portion in an upper end surface of the rib, the portion located in the central region of the bracket body and having sufficient strength can be used as the fulcrum portion for applying the operating force.

PREFERRED EMBODIMENTS OF THE INVENTION

Figure 1:
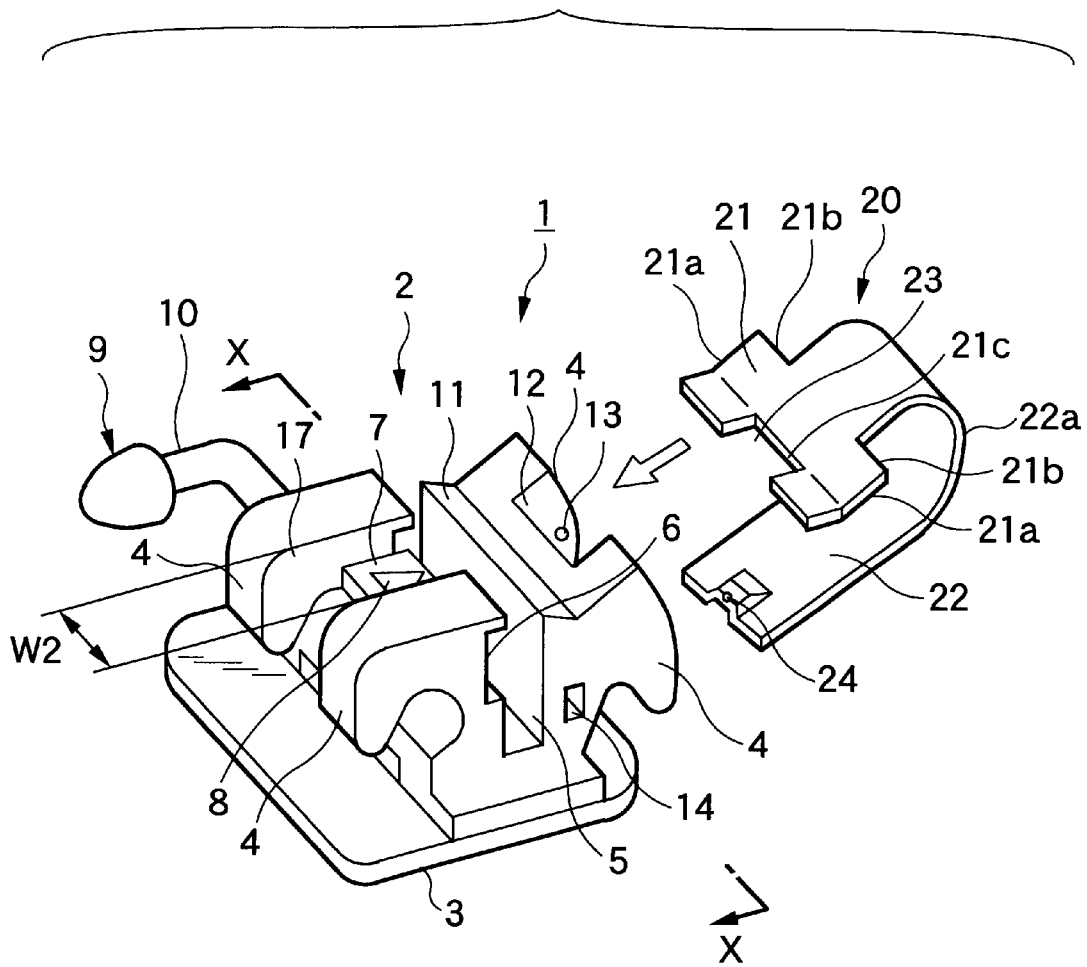
FIG. 1 is an exploded perspective view of an orthodontic bracket in accordance with the invention.

Referring now to the drawings, a detailed description will be given of the embodiments of an orthodontic bracket in accordance with the invention.

Figure 2:
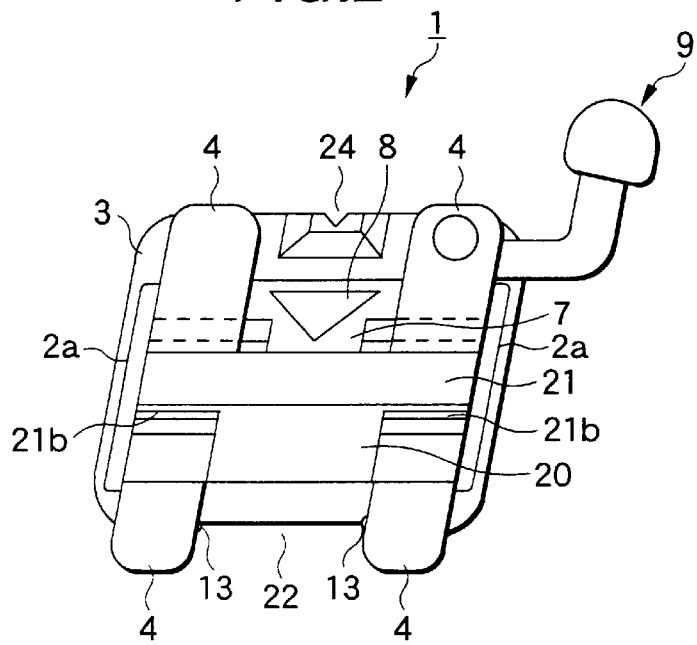
FIG. 2 is a plan view of the orthodontic bracket in accordance with the invention.
Figure 3A:
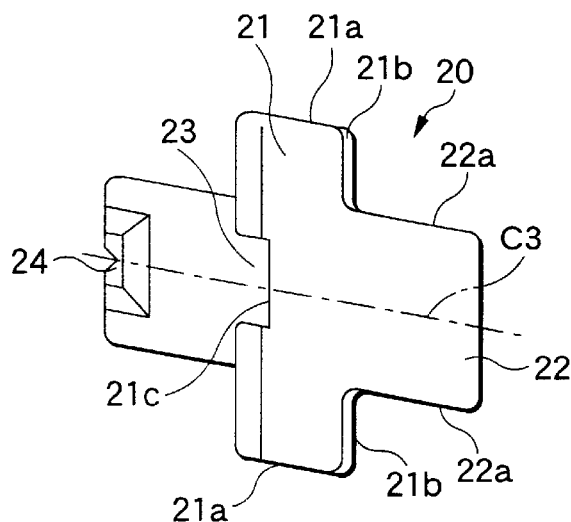
FIG. 3 is a plan view and a side elevational view of a locking member of the orthodontic bracket in accordance with the invention.
Figure 3B:
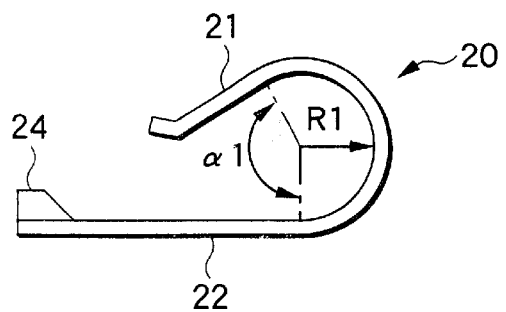

FIG. 1 is an exploded perspective view of a first embodiment of the orthodontic bracket in accordance with the invention. FIG. 2 is a plan view of the orthodontic bracket in accordance with the invention. FIGS. 3A and 3B are a plan view and a side view of a locking member of the orthodontic bracket in accordance with the invention.

Figure 4:
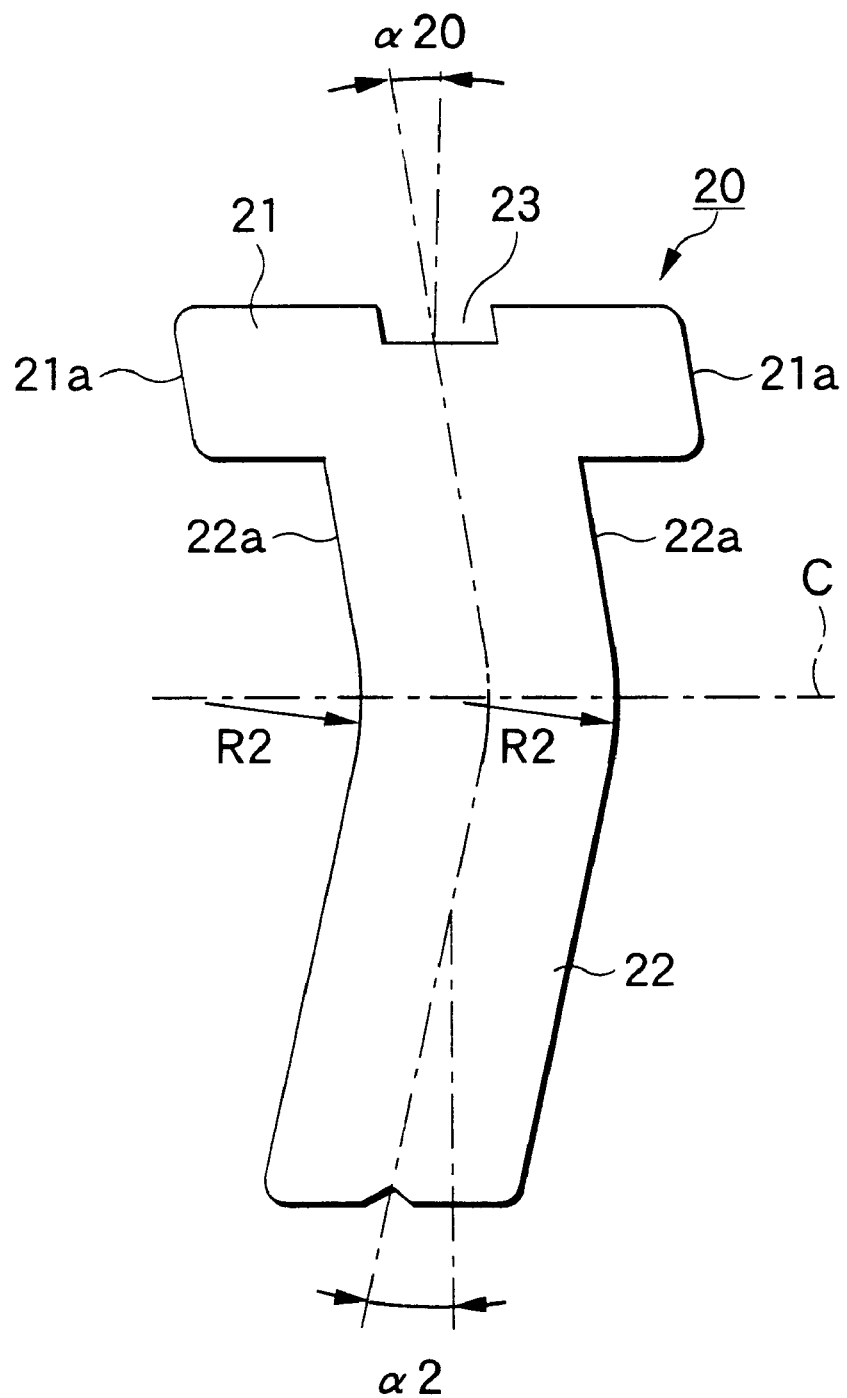
FIG. 4 is a development view of the locking member of the orthodontic bracket in accordance with the invention.

FIG. 4 is a development view of the locking member of the orthodontic bracket in accordance with the invention.

Figure 5:
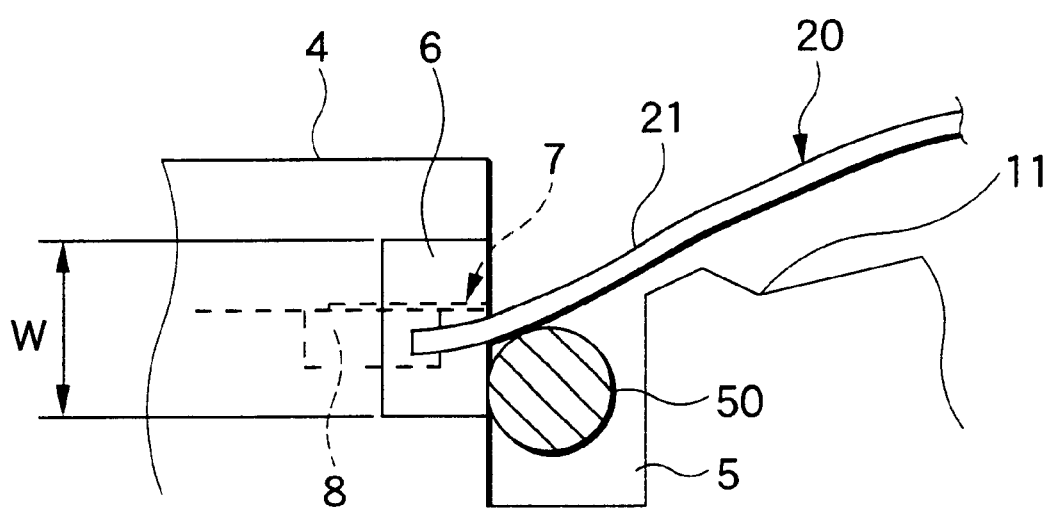
FIG. 5 is a schematic cross-sectional view for explaining the operation of the locking member and a rib of the orthodontic bracket in accordance with the invention.

FIG. 5 is a schematic cross-sectional view for explaining the operation of the locking member and a rib of the orthodontic bracket in accordance with the invention.

Figure 6:
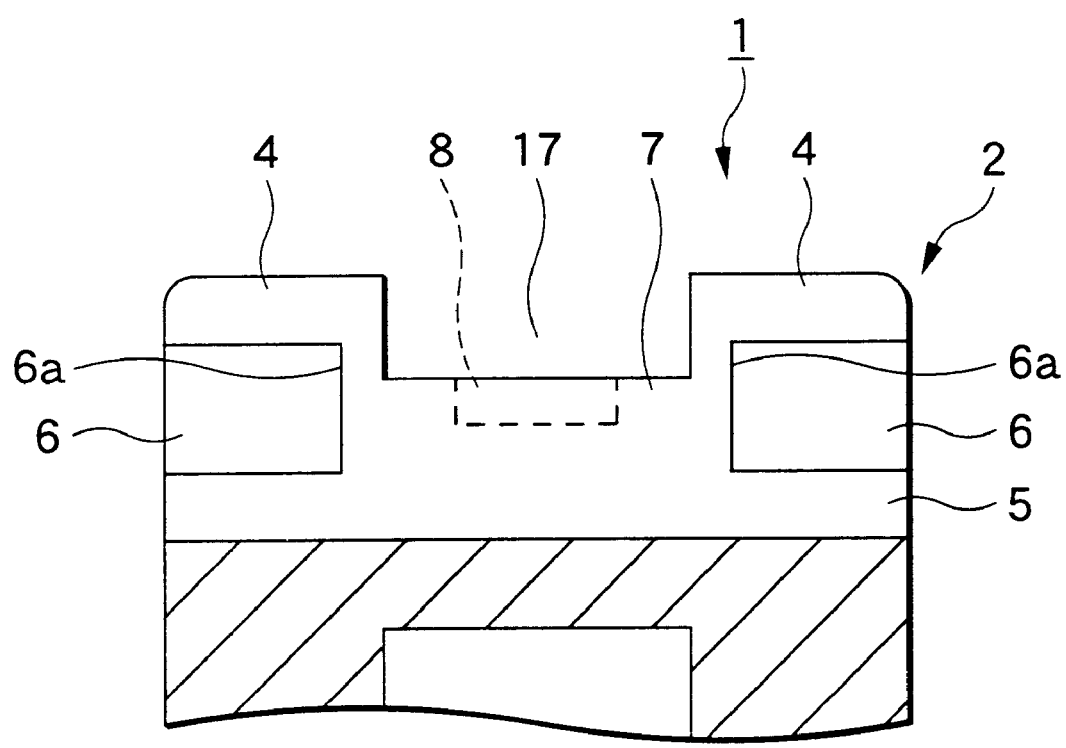
FIG. 6 is a cross-sectional view of modified example of the portion.
Figure 7:
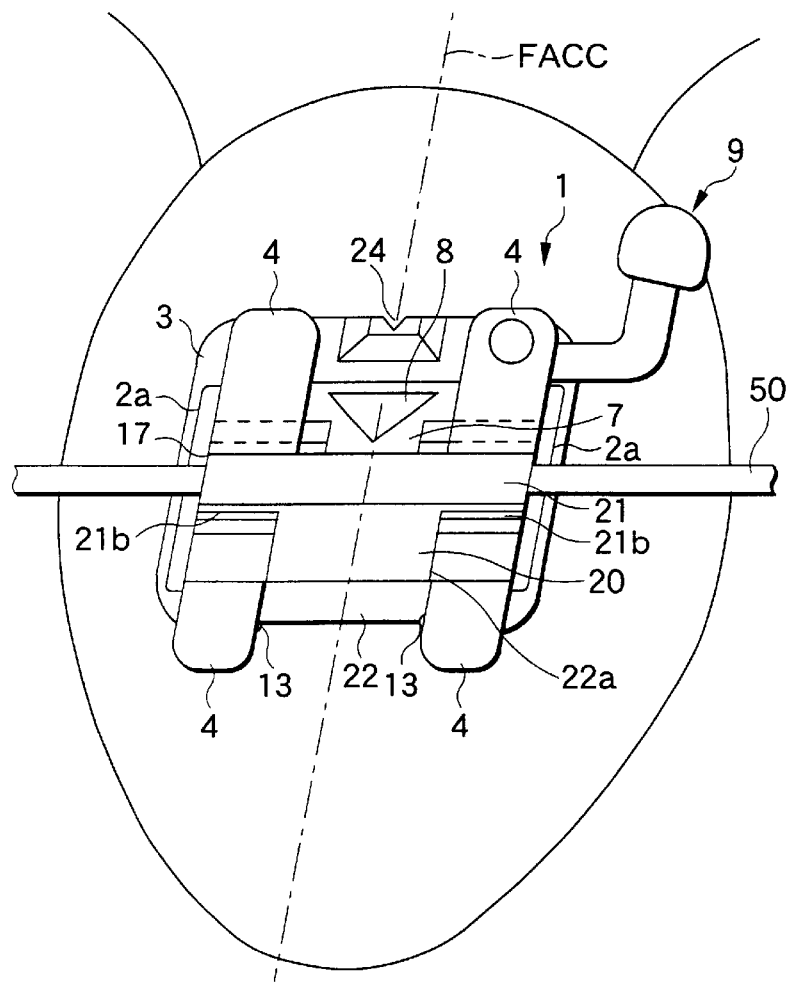
FIG. 7 is a plan view illustrating a fitted state of the orthodontic bracket in accordance with the invention.
Figure 8:
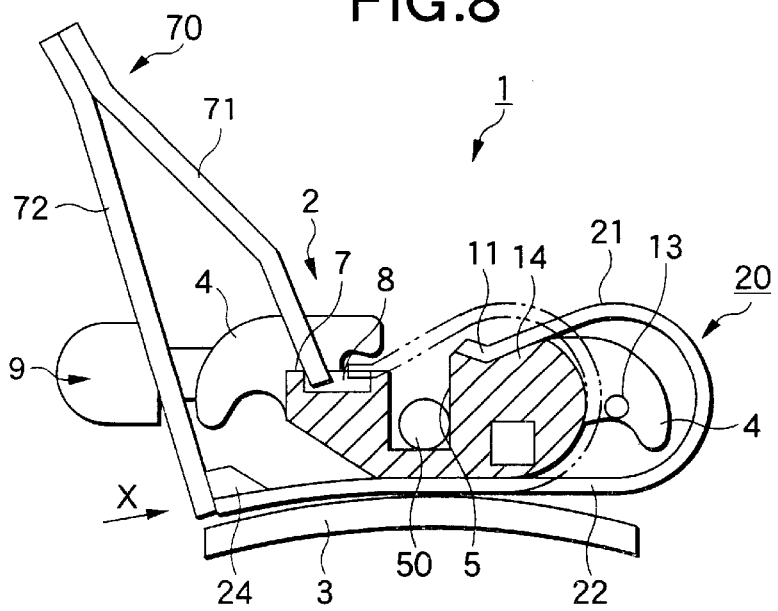
FIG. 8 is a schematic side elevational view for explaining the operation of the orthodontic bracket in accordance with the invention and the operation of a tool for the orthodontic bracket in accordance with a second embodiment.

FIG. 6 is a cross-sectional view of modified example of the portion taken along line X—X in FIG. 1. FIG. 7 is a plan view illustrating a fitted state of the orthodontic bracket in accordance with the invention. FIG. 8 is a schematic side elevational view for explaining the operation of the orthodontic bracket in accordance with the invention and the operation of a tool for the orthodontic bracket in accordance with a second embodiment.

Figure 9:
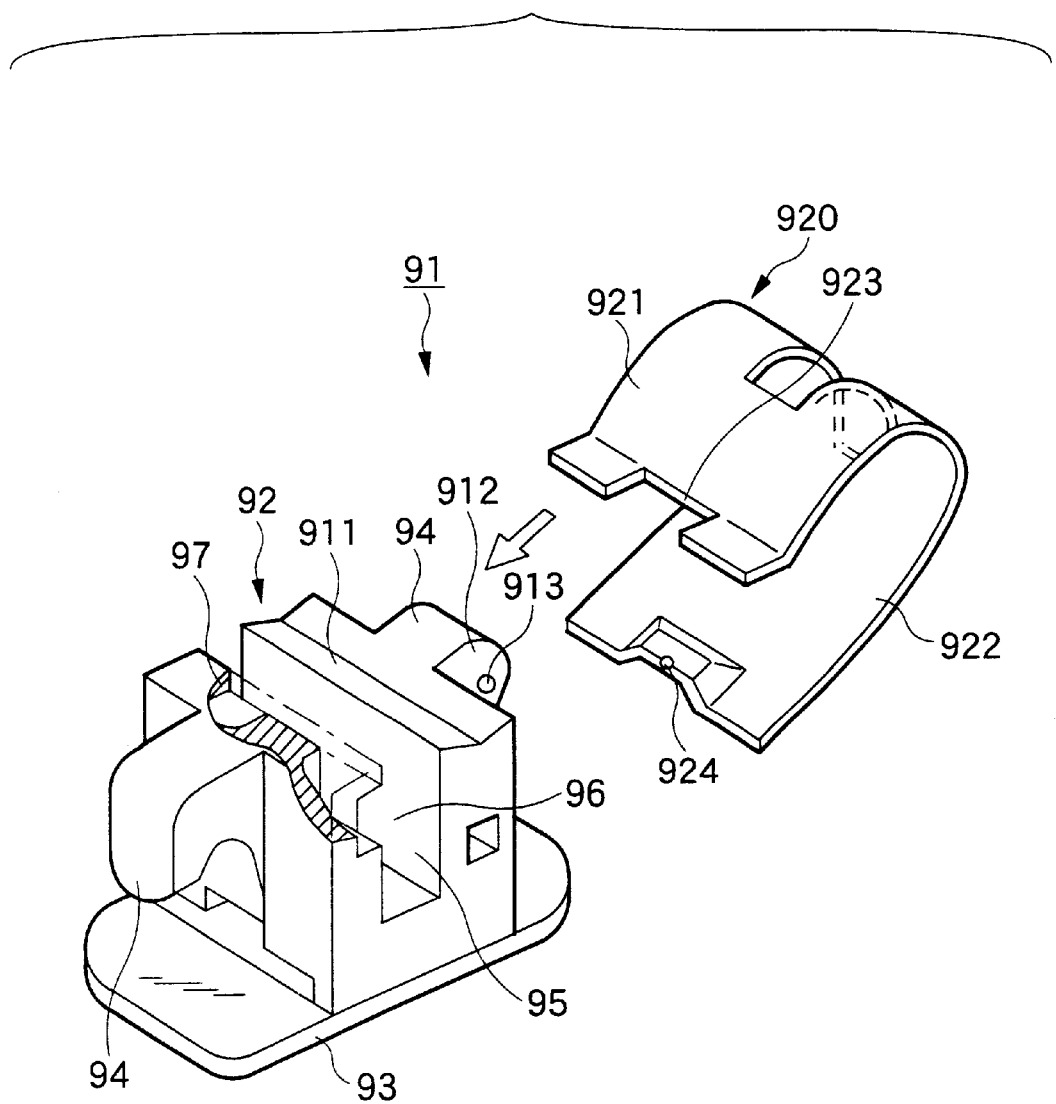
FIG. 9 is an exploded perspective view of the orthodontic bracket in accordance with a third embodiment of the invention.

FIG. 9 is an exploded perspective view of the orthodontic bracket in accordance with a third embodiment of the invention.

Figure 10A:
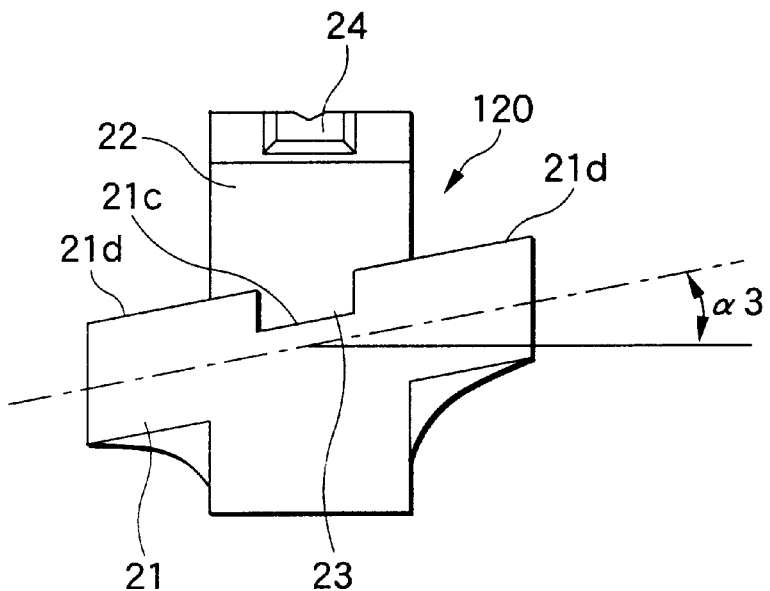
FIGS. 10A and 10B are plan views of the orthodontic bracket in accordance with a fourth embodiment of the invention.
Figure 10B:
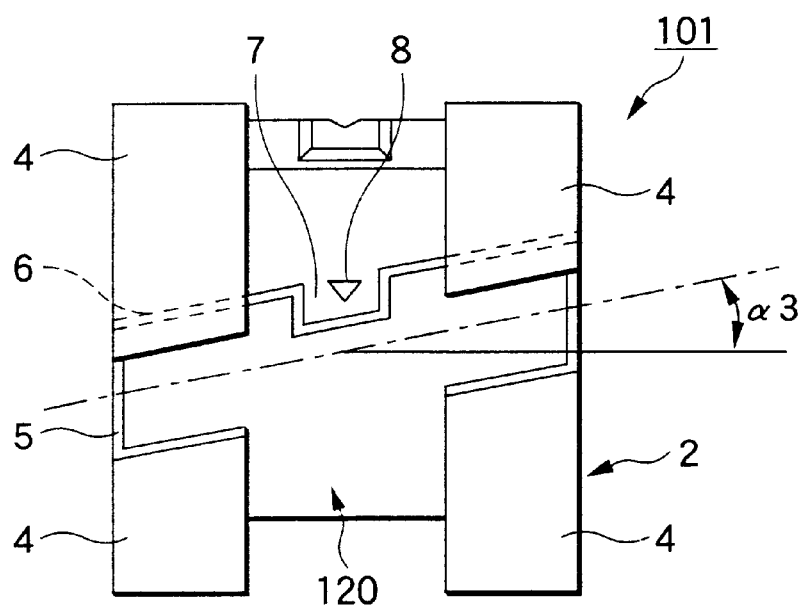

FIGS. 10A and 10B are plan views of the orthodontic bracket in accordance with a fourth embodiment of the invention.

Figure 11:
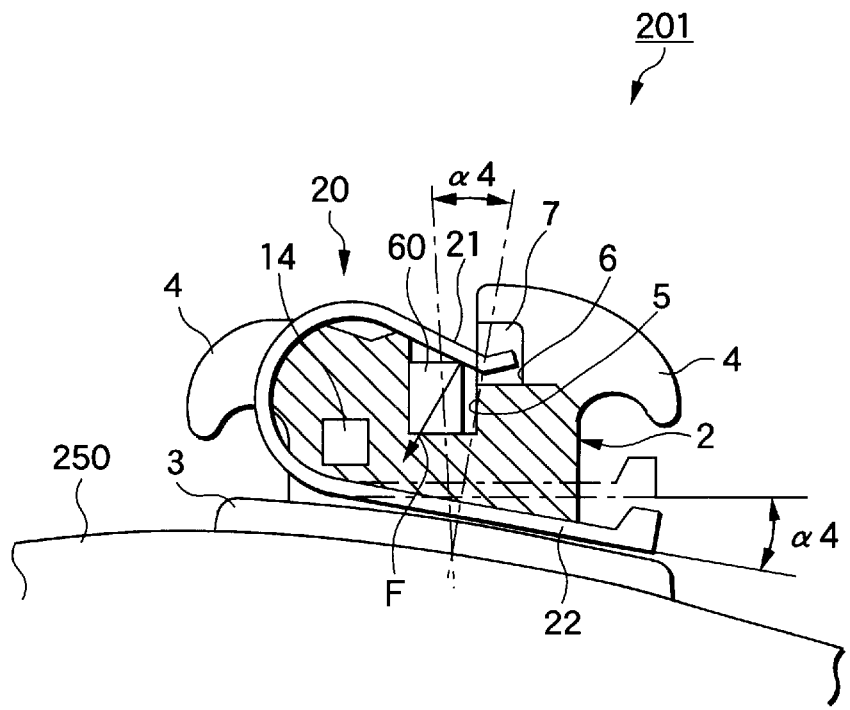
FIG. 11 is a schematic side elevational view of the orthodontic bracket in accordance with a fifth embodiment of the invention.

FIG. 11 is a schematic side elevational view of the orthodontic bracket in accordance with a fifth embodiment of the invention.

Figure 12:
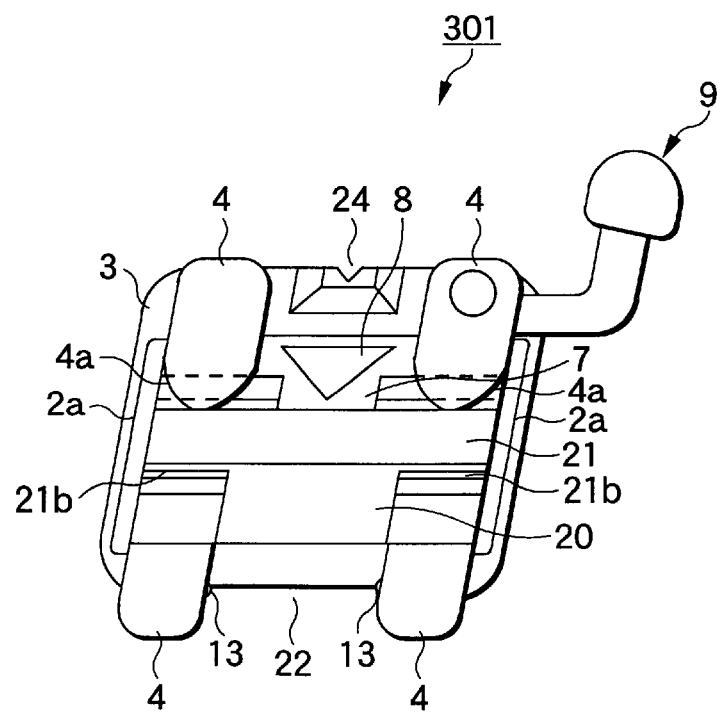
FIG. 12 is a schematic plan view of the orthodontic bracket in accordance with a sixth embodiment of the invention.
Figure 13:
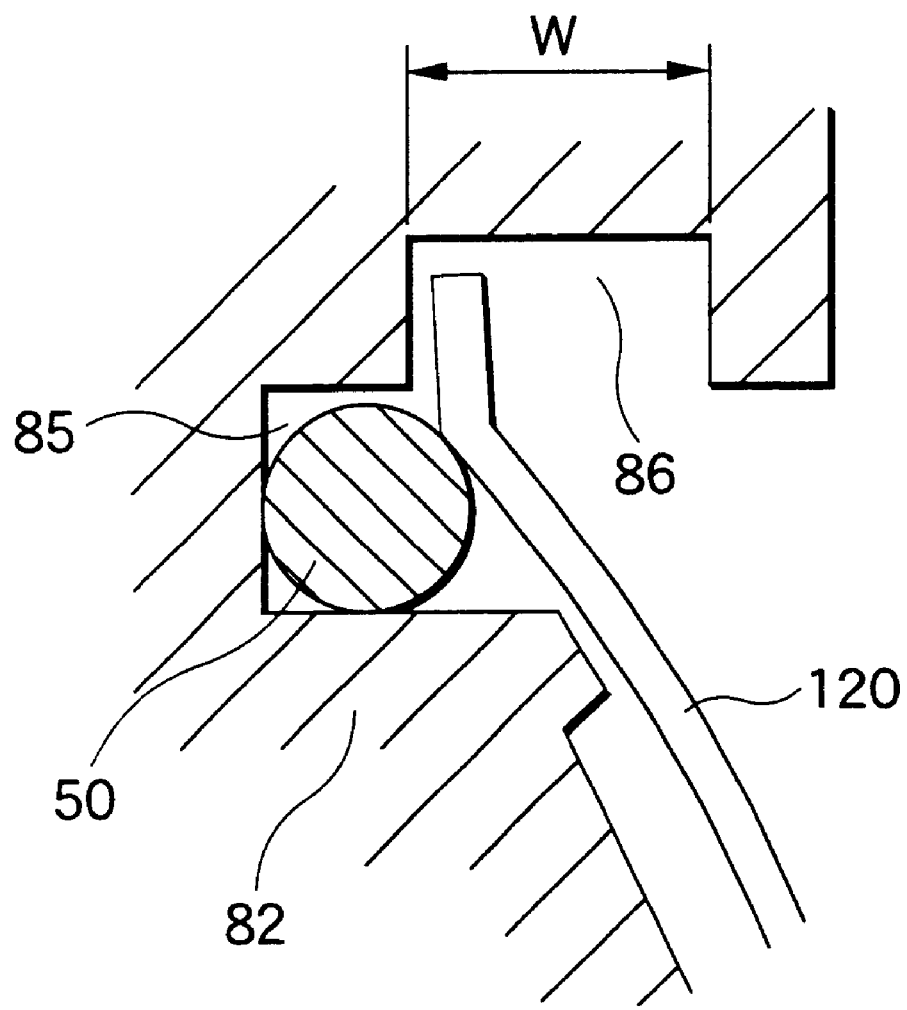
FIG. 13 is a partial cross-sectional view illustrating the action of the locking member in a normal state of an arch wire in a conventional orthodontic bracket.
Figure 14:
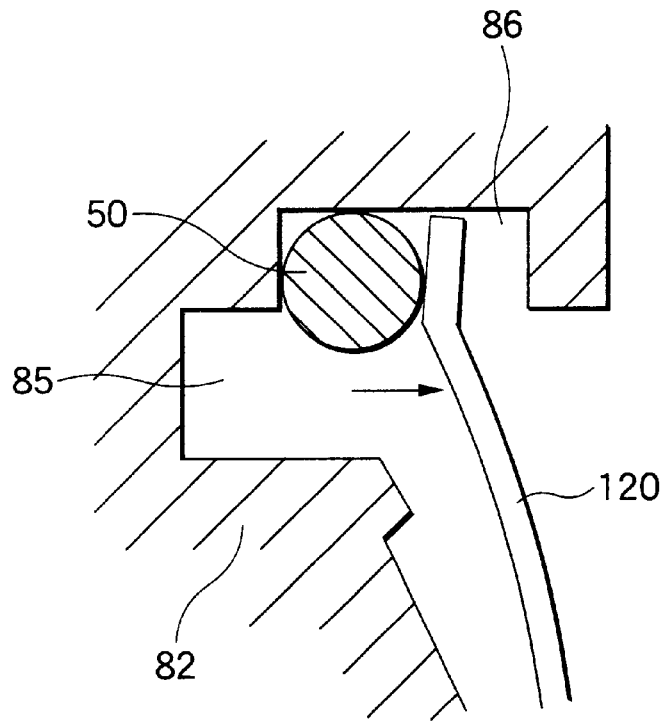
FIG. 14 is a partial cross-sectional view illustrating the state when the arch wire has shifted in the conventional orthodontic bracket.
Figure 15:
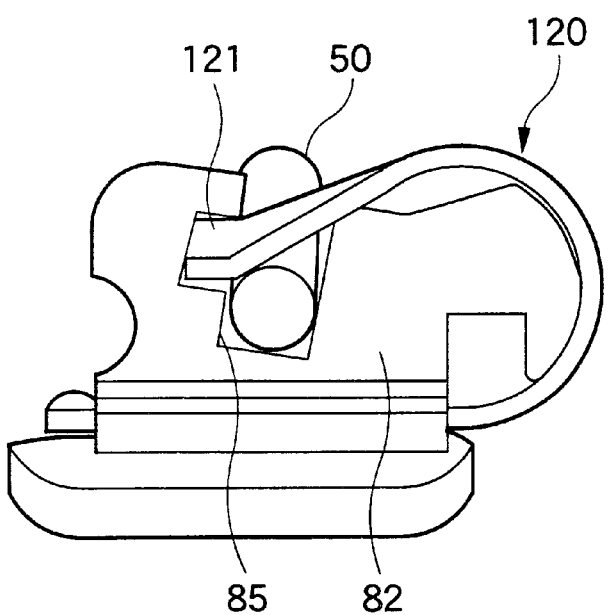
FIG. 15 is partial cross-sectional view illustrating the state of the locking member when the arch wire has shifted in the conventional orthodontic bracket.

FIG. 12 is a schematic plan view of the orthodontic bracket in accordance with a sixth embodiment of the invention.

(First Embodiment)

An orthodontic bracket 1 in accordance with the first embodiment shown in FIGS. 1 and 2 is a twin bracket having a central groove 17 enclosed by mesial tie wings 4 and distal tie wings 4. This bracket 1 is provided with a base 3 secured to a tooth surface, a bracket body 2 extending in a substantially perpendicular direction from the base, and an arch wire slot 5 which extends in a mesiodistal direction substantially in the center of the bracket body 2 and is open in the front. The bracket 1 is provided with a locking member 20 capable of opening or closing the arch wire slot 5.

As shown in FIGS. 1 and 3, this locking member 20 is structured in a substantially U-shaped cross-sectional configuration, and one side thereof is formed as a base side portion 22 (a portion located on the lingual side) located on the base side and extending along the base, while the other side thereof is formed as a counter base side portion 21 having substantially the same width as the length of the arch wire slot 5 and extending on the upper side of the slot. The locking member 20 is formed of an elastic member in which a notched portion 23 is provided substantially in the center of a tip edge portion of the counter base side portion 21 (a portion located on the labial side).

Meanwhile, a stop groove 6 for stopping a tip of the locking member 20 at a slot closed position is formed in the bracket body at an open edge portion of the arch wire slot 5. Further, an open stop concavity 11 for stopping the tip of the locking member 20 in a slot open position is formed at an edge portion thereof located away from the stop groove 6. A rib 7 projecting to bury the stop groove 6 in correspondence with the notched potion 23 is formed in a longitudinally central portion of the stop groove 6.

In addition, a recessed portion 8 of, for instance, a triangular shape is formed on an upper end surface of the rib 7. Further, an engaging end portion 24, which can be formed by a notched portion, a recessed portion, a projection, or the like, is formed at a rear end portion of the base side portion 22 in the locking member 20.

Further, an opening 14 extending along the arch wire lot 5 (in the mesiodistal direction) is penetratingly formed in the bracket body 2. This opening 14 can be used by allowing a ligating member to be passed therethrough when the locking member 20 is to be fixed more firmly.

Further, the bracket body 2 is provided with a pair of projections 13 at positions corresponding to both side edge portions of a curved portion of the locking member 20. These projections 13 project to such an extent that they can abut against the side curved portion between the locking member 20 and 21 both edge portions 22a of the curved portion with appropriate pressure. The arrangement provided is such that when the locking member 20 has closed the arch wire slot 5, these projections 13 are located on the outer sides of both side edge portions of the curved portion.

Accordingly, for instance, even when an unexpected external force has been applied in the oral cavity, these projections 13 hold down the base side portion 22, thereby suppressing the shift of the locking member 20 in the opening direction.

In the orthodontic bracket 1 constructed as described above, the locking member 20 is capable of sliding smoothly on the bracket body 2 so as to open or close the arch wire slot 5. Then, since the rib 7 corresponding to the notched portion 23 in the locking member 20 is formed in the longitudinally central portion of the stop groove 6, even if the height W of the stop groove 6 is formed to be larger than the diameter of an arch wire 50, it is possible to prevent a situation in which the arch wire 50 enters the stop groove 6 when the arch wire 50 is urged so as to be lifted up from the bottom of the slot 5, as shown in FIG. 5.

In addition, since the notched portion 23 at the tip portion of the locking member 20 is engaged so as to be fitted in the widthwise central portion of the stop groove 6, the counter base side portion 21 can be held firmly, so that it is possible to prevent the deviation of the counter base side portion 21 in the longitudinal direction of the slot, and the twisting of the counter base side portion 21. Further, since the tip portion of the counter base side portion 21 is stopped by the stop groove 6, the locking member 20 does not open unintentionally toward the labial side.

It should be noted that the form shown in FIGS. 5 and 6 shows a structure different from that of the form shown in FIGS. 2 and 3. Namely, in the form shown in FIGS. 5 and 6, the height of the stop groove 6 is set to be larger than the height of the rib 7. Furthermore, as shown in FIG. 6, the width of the stop groove 6 in the mesiodistal direction is set to be smaller than the width of the tie wing 4, and a side wall 6a of the stop groove 6 is connected to the tie wings Further, the bracket body 2 is provided with a hook 9 whose proximal portion 10 projecting out in the lateral direction (toward the distal side) from the body 2. If this arrangement is provided, for example, when a tool 70 (see FIG. 8) is engaged with the bracket body 2 as will be described later, no hindrance is caused to the operating efficiency.

In addition, in the orthodontic bracket 1 in this embodiment, in a case where the locking member 20 is formed of a superelastic member such as a nickel-titanium alloy, even if the locking member has been deformed relatively greatly, there is no large variation of the load, and the arch wire can be pressed down moderately under the superelasticity. Additionally, favorable operating efficiency in the treatment operation can be maintained. For example, wires ranging from a narrow round wire to a full-sized square wire can be pressed into the slot with a virtually equivalent load, and three-dimensional control becomes possible starting from an early period of treatment with an optimum force in the living body. In addition to the restoring force of the wire, the correcting force is also produced by the force with which the locking member presses down the arch wire, and treatment of higher dimensionality becomes possible.

In addition, in the orthodontic bracket 1 in accordance with this embodiment, if the locking member 20 is formed of a beta titanium alloy, a Co—Ni-base alloy of high Cr and high Mo, or a work-hardening Ni—Ti alloy, it is possible to enlarge the pressing force (load) relative to the amount of deformation, so that the slot can be sealed reliably and the arch wire can be pressed positively. Further, if the locking member 20 is formed of a β•titanium alloy, a Co—Ni-base alloy of high Cr and high Mo, or a work-hardening Ni—Ti alloy, although the locking member 20 does not exhibit the property of superelasticity such as that of the nickel-titanium alloy, since the narrow round wire is not pressed down, a totally friction free state is obtained, thereby attaining efficient shift of the tooth.

As the above-described Co—Ni-base alloy of high Cr and high Mo, it is possible to use one which contains, for example, approx. 39.25 wt.% of cobalt, 15.70 wt.% of nickel, 19.95 wt.% of chromium and the balance essentially consisting of iron and the like.

As shown in FIG. 4, the locking member 20 of the orthodontic bracket 1 in this embodiment can be formed by using a single substantially T or Y-shaped plate as its raw material. For example, an unillustrated plate material is formed into a substantially T or Y-shaped configuration by blanking or the like, and is then formed by bending as described below.

As for the formation of the locking member 20, in a developed state upper and lower portions of the locking member 20 in the substantially T or Y-shaped configuration with a substantially longitudinally central portion C thereof as a boundary are respectively bent with a predetermined angle α2 of about 10 degrees in the base of a bracket for an upper jaw canine tooth, for example.

To give a more detailed description of the locking member 20, a portion of the base side portion 22 located close to the base with the substantially longitudinally central portion as the boundary is set at an angle of inclination α2 (an angle of 10 degrees or thereabouts) conforming to the angulation of the bracket, while the counter base side portion 21 on the opposite side away from the side close to the base is set at an angle of inclination α20 (8 degrees or thereabouts) which is obtained by correcting an angle corresponding to a bent portion for pressing the arch wire in addition to the angle of inclination (10 degrees) of the bracket angulation. In addition, a curved portion connecting the base side portion 22 and the counter base side portion 21 forms a portion of a sine curve.

As for the relationship between the radius of curvature R2 (see FIG. 4) of this curved portion and the radius of curvature R1 (see FIG. 3B) of the base side portion 22 in the thicknesswise direction, as shown in FIG. 3A, in a top view of the locking member 20 the left and right edge portions 22a of the curved portion located on the inner sides of the tie wings 4 are correspondingly formed to be seen as straight lines parallel to a center line C3.

Accordingly, in the case where the shape of the bracket body 2 is of the rhomboid type, as shown in FIG. 7, the line of the aforementioned edge portion 22a can be made to conform with the facial axis of the clinical crown (FACC) in cooperation with the mesial and distal side surfaces of the bracket body 2 and the central groove 17, thereby facilitating the alignment of the bracket.

Thus, in the orthodontic bracket 1 in this embodiment, left and right edge portions 21a of the counter base portion 21, which is the T or Y-shape head portion in the substantially T or Y-shaped configuration of the locking member 20, and the left and right edge portions 22a of the curved portion, in a top view of the bracket, are formed in parallel along mesial and distal ends of the bracket body flange 2a. In addition, the locking member 20 can be mounted such that, as a rough criterion, edge portions of the counter base portion 21 extending along the mesiodistal direction become parallel to the occlusal surface or the arch wire line.

(Second Embodiment)

A description will be given of a tool for an orthodontic bracket which is used for the orthodontic bracket 1 shown in the above-described first embodiment.

The tool 70 for an orthodontic bracket in this embodiment is not particularly limited to the illustrated form insofar as a first arm portion 71 and a second arm portion 72 are arranged to be appropriately continuous as shown in FIG. 8, and it is possible to adopt various forms.

In short, the tool 70 for an orthodontic bracket includes the first arm portion 71 which is a fulcrum portion for engagement with the bracket body 2 (in this embodiment, the recessed portion 8 in the upper end surface of the rib 7 provided on the bracket body 2), and the second arm portion 72 which serves as an acting portion for engagement with the engaging end portion 24 (e.g., a notched portion, a recessed portion, a projection, or the like) formed at the rear end portion of the base side portion 22 in the locking member 20.

Since the tool 70 for an orthodontic bracket is structured as described above, by using the recessed portion 8 in the upper end surface of the rib 7 as the fulcrum and the engaging end portion 24 at the rear end portion as the point of application, by pushing the engaging end portion 24 in the X direction as in the illustrated case it is possible to shift the entire locking member 20 in the X direction, thereby effecting the opening operation of the arch wire slot 5. Consequently, the locking member 20 is held in a stopped state as its counter base portion 21 is located in such a manner as to be fitted in the open stop concavity 911.

The closing operation of the locking member 20 (the operation in a direction opposite to the X direction) can be effected by pushing the curved portion in a direction opposite to the X direction. It should be noted that, in this pressing operation, the completion of the closing operation of the locking member 20 can be recognized by the clicking operation when the left and right edge portions 22a of the curved portion ride over the projections 13 in a terminating stage of the pressing operation.

(Third Embodiment)

Referring now to FIG. 9, a description will be given of a third embodiment of the invention.

An orthodontic bracket 91 in accordance with the third embodiment shown in FIG. 9 is a single bracket in which a bracket body 92 has a pair of tie wings 94, and this bracket 91 is consisting of a base 93 secured to a tooth surface, a bracket body 92 extending in a substantially perpendicular direction from the base 93, and an arch wire slot 95 which extends in the mesiodistal direction substantially in the center of the bracket body 92 and is open in the front. The bracket 91 is provided with a locking member 920 capable of opening or closing the arch wire slot 95.

This locking member 920 has on one side thereof a base side portion 922 located on the base side and extending along the base, and on the other side thereof a counter base side portion 921 having substantially the same width as the length of the arch wire slot 95 and extending on the upper side of the slot. The locking member 920 has in its curved portion a hole from which the tie wing is exposed during the closing of the slot. The locking member 920 is formed of an elastic member in which a notched portion 923 is provided substantially in the center of a tip edge portion of the counter base side portion 921 (a portion located on the labial side).

Meanwhile, a stop groove 96 for stopping a tip of the locking member 920 at a slot closed position is formed in the bracket body 92 at an open edge portion of the arch wire slot 95. Further, an open stop concavity 911 for stopping the tip of the locking member 920 in the slot open position is formed at an edge portion thereof located away from the stop groove 96. A rib 97 projecting to bury the stop groove 96 in correspondence with the notched potion 923 is formed in a longitudinally central portion of the stop groove 96.

In addition, projections 913 are respectively provided on both mesial and distal side surfaces 912 of one tie wing 94. These projections 913 project to such an extent that they can abut against the curved portion of the leg of the locking member 920 with appropriate pressure. Accordingly, when the locking member 920 has closed the arch wire slot 95, these projections 913 are located on the outer sides of locking member 920. Consequently, even when an unexpected external force has been applied in the oral cavity, these projections 913 suppress the shift of the locking member 920 in the opening direction.

(Fourth Embodiment)

Referring now to FIGS. 10A and 10B, a description will be given of a fourth embodiment of the invention. It should be noted that, in the description of a bracket body 101 and a locking member 120 in this embodiment, these members are similar to those of the first embodiment except that they are of a cut-angulation type, and constituent elements similar to those of the first embodiment will be denoted by the same reference numerals, and a description thereof will be omitted, as necessary.

In an orthodontic bracket 101 in this embodiment, as shown in FIG. 10B, the bracket body 2 is of a cut-angulation type in which, in a plan view, the arch wire slot 5 is inclined ($\alpha 3$) with respect to a substantially square contour of the bracket.

Further, an arrangement is provided such that, as shown in FIG. 10A, a pair of tip edge portions 21d of the counter base side portion 21 of the locking member 120, 21d, and an innermost edge portion 21c of the notched portion 23 become parallel to the arch wire slot 5.

Accordingly, the leg of the locking member 120 is not provided with an inclination such as $\alpha 2$ and $\alpha 20$ (see FIG. 4) and a curve such as R2 and is straight, but the T or Y-shape head portion (the counter base side portion) is inclined by an angle of $\alpha 3$.

It should be noted that, with the cut angulation type, if the angulation (angle $\alpha 3$) is large, the strength of the tie wings drops, but since the rib 7 is formed, a reinforcing effect is provided. Further, if the angulation (angle $\alpha 3$) is large, the shape becomes large, but there is an advantage in that positioning on the crown is facilitated as compared to the rhomboid type.

(Fifth Embodiment)

Referring now to FIG. 11, a description will be given of a fifth embodiment of the invention.

It should be noted that a bracket body 201 in this embodiment is similar to that of the first embodiment except that it has a torque-in-base structure, and a description thereof except for the characteristic portion of this embodiment will be omitted, as necessary.

The orthodontic bracket 201 in this embodiment has the so-called torque-in-base structure in which the base 3 is inclined with respect to the upper structure of the bracket body 2 (i.e., a structure in which when the side walls of the arch wire slot 5 are parallel to the occlusal surface, the base 3 is inclined by a crown inclination angle of $\alpha 4$ at a point FA (see FIG. 11)). This torque-in-base structure is not a structure in which the arch wire slot 5 is formed in an inclined manner, the pressing direction (in the F direction) of the tip portion of the locking member 20 with respect to a square arch wire 60 becomes stabilized.

By having the inclination angle of $\alpha 4$ corresponding to the torque, the locking member 20 has an opening angle between the base side portion 22 and the counter base side portion 21. Further, the distance between the base side portion 22 and the counter base side portion 21 (or the size of R1) changes in correspondence with the height of the bracket corresponding to the in/out of the dentition.

In the locking member 20, the direction of the load for pressing the square arch wire 60 into the slot becomes stabilized. As a result, it is possible to maintain a stable pressing force, so that an effect of accurate treatment can be expected.

Since the above-described structure is adopted, even in a case where a plurality of bracket bodies of different forms are used, since the relationship between the arch wire and the locking member can be fixed in any case, it is easy to estimate the treatment effect.

In addition, in the torque-in-base structure, the base side portion of the locking member is formed in such a manner as to be located in parallel to the base inclined in correspondence with the torque (with an inclination angle of $\alpha 4$), and is close to the bonding base in any case of the torque. Accordingly, the tip portion of the base side portion is not located so as to block the space below the tie wings, so that the amount of food residue stuck can be reduced, thereby making it possible to maintain oral hygiene in a favorable state.

Further, since the base side portion of the locking member is arranged to shift over the bonding base, the base side portion in any position is held by the base. Even in a case where the operation of strongly pressing its rear end by a tool is effected, the base side portion is able to open stably without becoming deformed.

(Sixth Embodiment)

Referring now to FIG. 12, a description will be given of a sixth embodiment of the invention.

It should be noted that a bracket body 301 in this embodiment is similar to that of the first embodiment except for the shape of the tie wings, and a description thereof except for the characteristic portion of this embodiment will be omitted, as necessary.

As for the tie wing 4 in this embodiment, an end face 4a on the arch wire slot side is formed in a tapered shape (or in a substantially conical shape or a chamfered shape). By adopting such a substantially conical shape or a chamfered shape, it is possible to avoid breakage or the like of the tip portion of the tie wing 4 during, for example, the replacement operation of the arch wire or the operation of the locking member 20.

(Seventh to Ninth Embodiments)

Seventh to ninth embodiments according to the present invention will be described as follows referring to FIGS. 16 to 18.

Incidentally, descriptions similar to the above described embodiments are omitted here, and the characteristic portions of these embodiments will be mainly described as follows.

Figure 16:
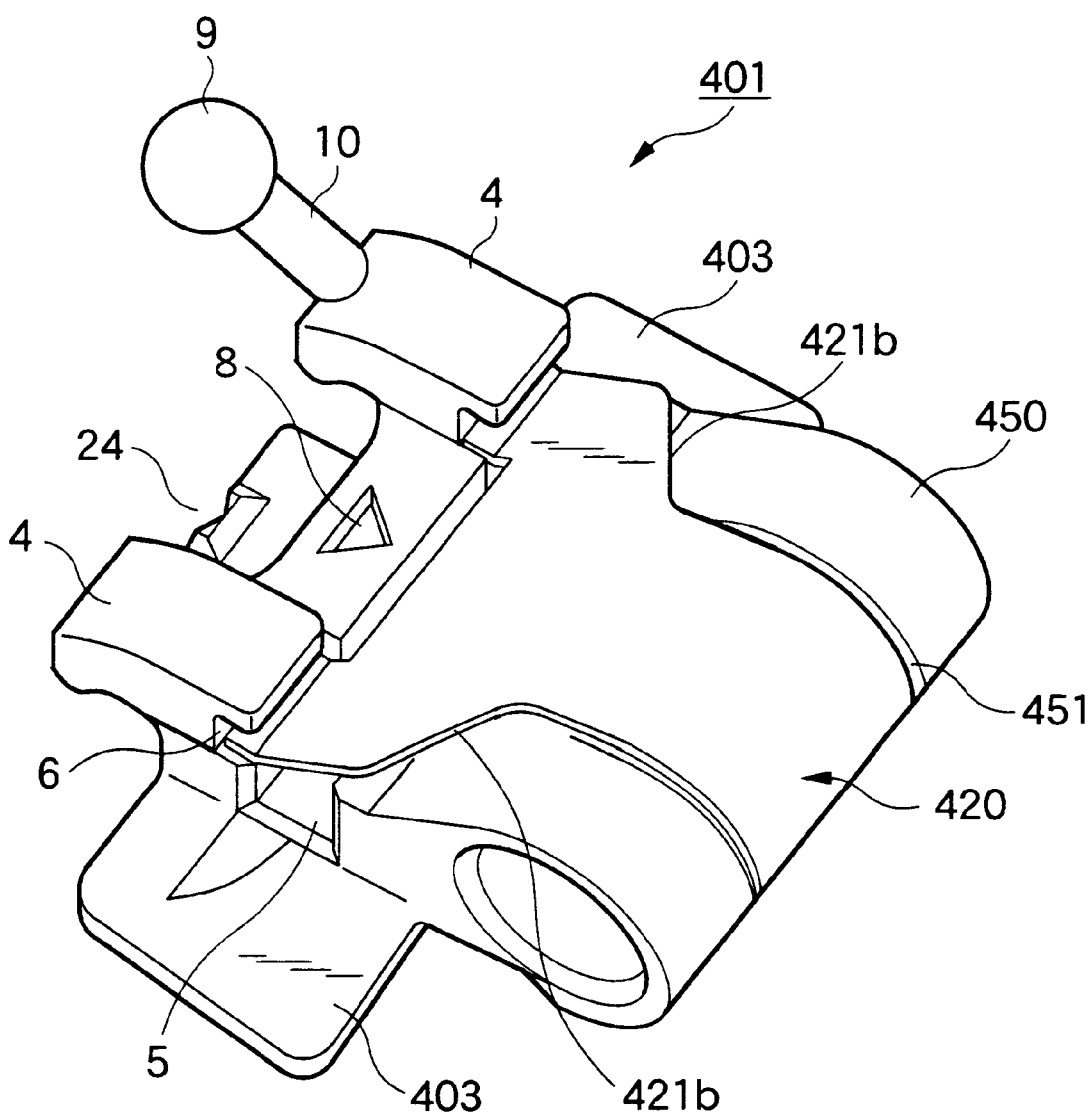
FIG. 16 is a perspective view showing a seventh embodiment according to the present invention.

FIG. 16 shows, for example, a double tube 401 weldable to an orthodontic band, which is provided with a cylindrical tube 450 in the occlusal side. This double tube 401 has a welding flange as a base portion. Further, the cylindrical tube 450 has a concavity portion 451 so that the lock member 420 is secured to the position on the cylindrical tube 450 when the lock member 420 is retained to the stop groove 6. Further, both edge portions 421b, 421b is formed to be curved.

Figure 17A:
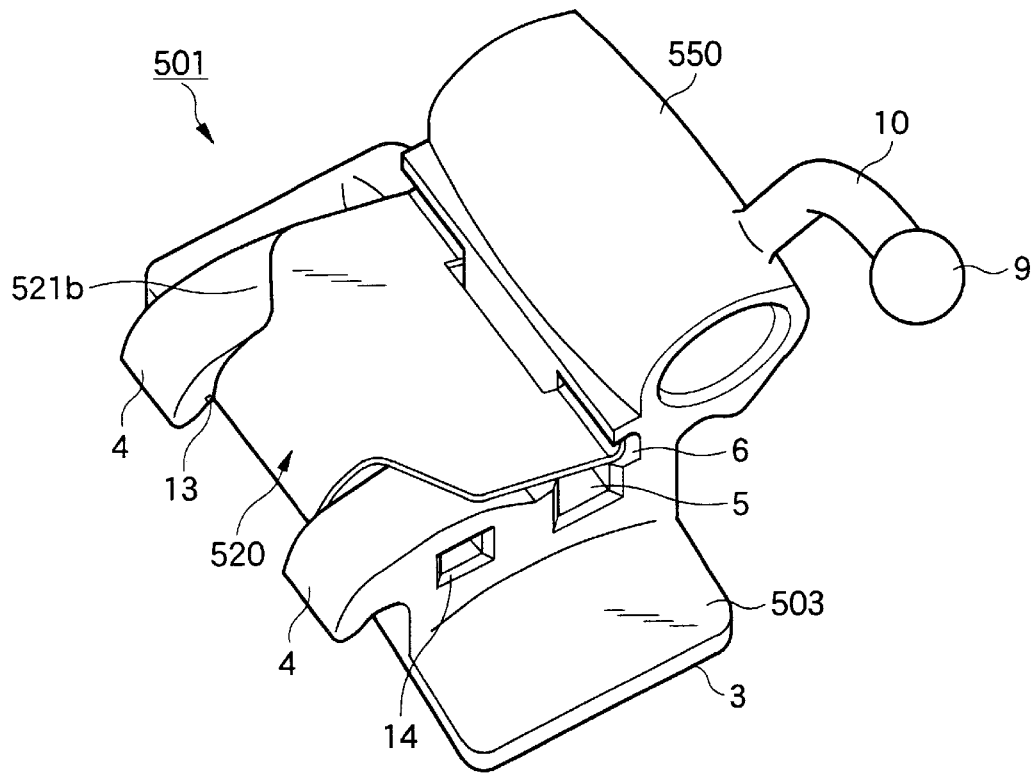
FIG. 17A is a perspective view showing an eighth embodiment according to the present invention.
Figure 17B:
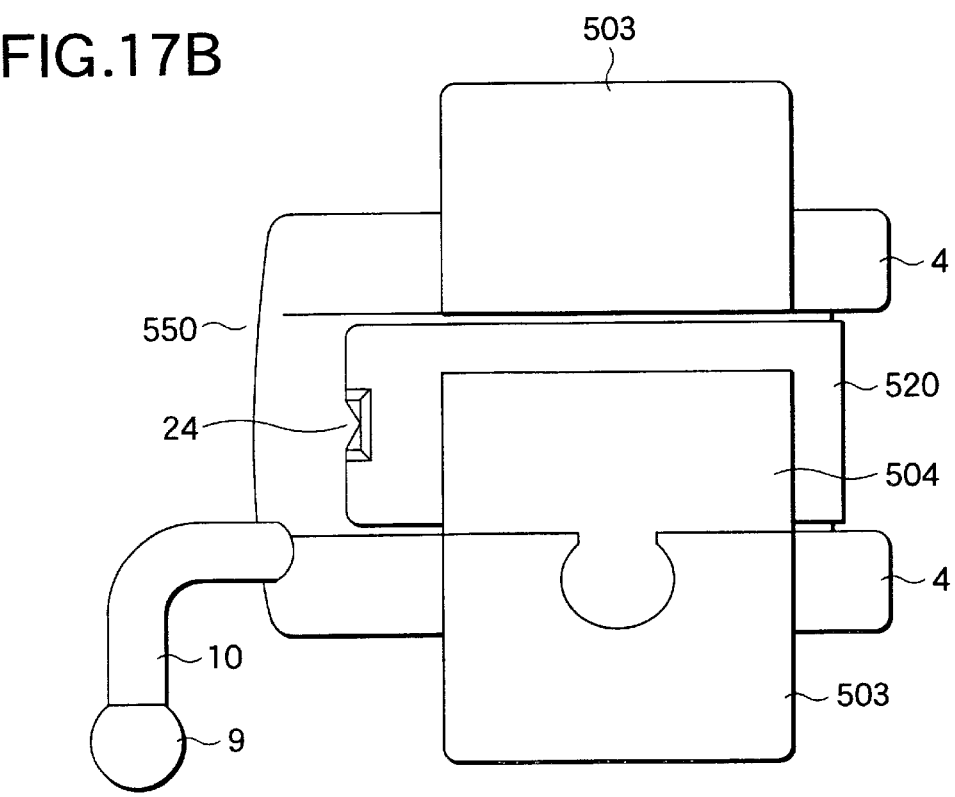
FIG. 17B is a bottom view showing the eighth embodiment according to the present invention;.

FIGS. 17A and 17B show, for example, a triple tube 501 having a cylindrical tube 550 in the gingival side. The triple tube has a welding flange 503 as a base portion. A cover member 504 is provided on the bottom of the triple tube 501 so as to secure the lock member 520.

Figure 18:
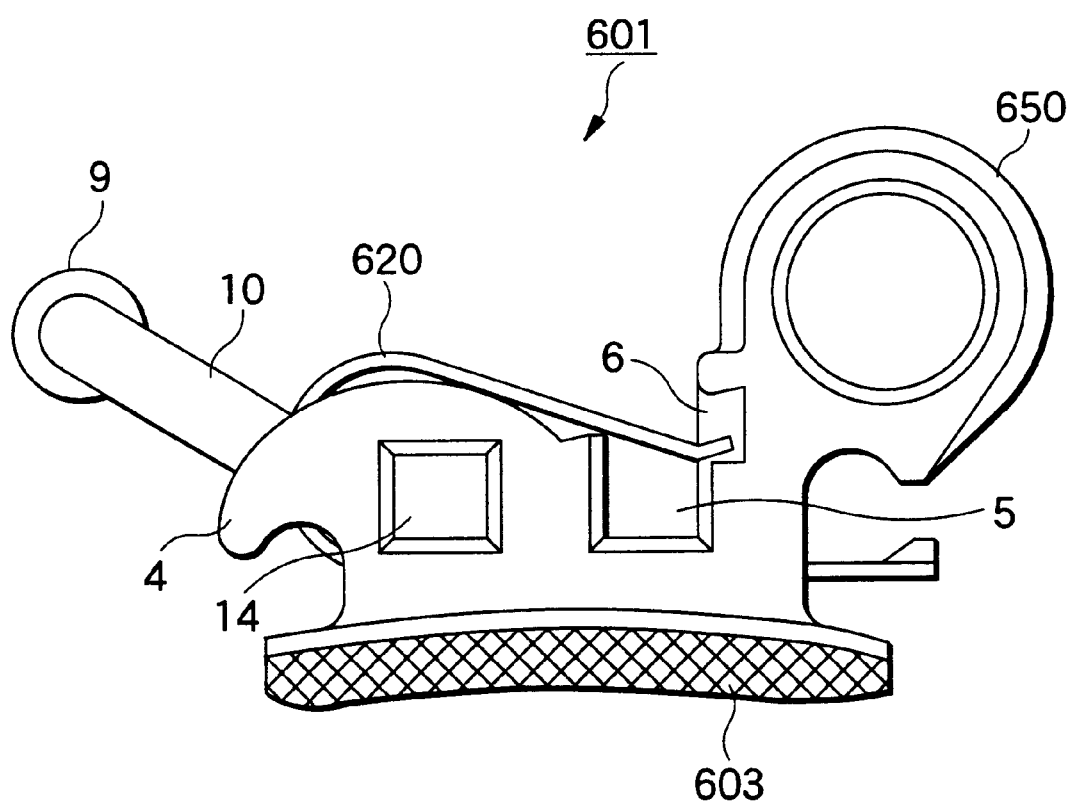
FIG. 18 is a front view showing a ninth embodiment according to the present invention.

FIG. 18 shows, for example, a bondable type triple tube 601 having a cylindrical tube 650 provided at the occlusal side, which is directly bonded to the surface of a tooth. This triple tube 601 has a bonding base 603 as a base portion.

The seventh to ninth embodiments are directed to a convertible buccal tube, which is a bracket mainly used for a first molar of upper and lower jaws. In this kind of bracket, a convertible cap is initially fixed while it covers the arch wire slot 5 by means of brazing or the like so as to form an angular tube. When second molars erupt with the growth of a patient, second molar tubes are attached to them to be uncollege teeth so that they are brought into the teeth arrangement arch to be treated. At this time, if the convertible cap of the tube bracket of the first molar is peeled off, and it is converted to a general bracket, the distal end of the arch wire can be inserted into a second molar tube. However, the peeling operation of the convertible cap in the mouth should be done carefully, and it is difficult to ligate the arch wire to the group of molars.

In the seventh to ninth embodiments, the lock member has the function of the distal end tube bracket of the upper and lower teeth arrangement in place of the convertible cap. This structure needs no ligature operation and has no convertible cap to be peeled off. In addition, when anterior teeth are retracted by a closing loop provided on the arch wire, it is necessary to be bent to prevent the distal end of the arch wire from pulling off from the arch wire bracket. However, it becomes possible to fit to the bracket previously by opening and closing the lock member. Thus, it is necessary to do a difficulty of the conventional tube bracket having the convertible cap, that is, the arch wire should be bent at the deep portion of the mouth after insertion, or it is pulled off after straightening.

What is claimed is:

1. An orthodontic bracket adapted to engage to a tooth surface, the orthodontic bracket comprising:
    a base adapted to engage the tooth surface;
    a bracket body extending in a substantially perpendicular direction from said base, said bracket body having an arch wire slot which extends in a mesiodistal direction substantially in a center of said bracket body;
    a locking member for opening or closing said arch wire slot;
    wherein said locking member, which is structured in a substantially U-shaped cross-sectional configuration, has a base side portion located on a base side and extending along said base and a counter base side portion having substantially the same width as the length of said arch wire slot and extending on an upper side of said slot, said locking member being formed of an elastic member, a notched portion being provided substantially in a center of said counter base side portion;
    wherein said bracket body has a closing stop groove formed at an open edge portion of said arch wire slot so as to stop a tip of said locking member in a slot closed position and an open stop concavity formed at an edge portion thereof located away from said stop groove so as to stop the tip of said locking member in a slot open position, a rib being formed in a longitudinally central portion of said stop groove in such a manner as to project so as to bury said stop groove in correspondence with said notched portion.

2. The orthodontic bracket according to claim 1, wherein said bracket body is a twin bracket having a central groove sandwiched between mesial tie wings and distal tie wings, and said rib is formed over an entire width of said central-groove and is formed in such a manner as to be connected to said mesial tie wing and said distal tie wing.

3. The orthodontic bracket according to claim 1, wherein said bracket body is a single bracket having at least one tie wing.

4. The orthodontic bracket according to claim 1, wherein said bracket body is a lingual bracket which is adapted to couple to a lingual side of the tooth.

5. The orthodontic bracket according to claim 1, wherein a recessed portion is formed in an upper end surface of said rib.

6. The orthodontic bracket according to claim 1, wherein an engaging end portion formed by a recess or a notch is formed at a rear end portion of said base side portion of the locking member.

7. The orthodontic bracket according to claim 1, wherein said bracket body has an opening extending therethrough along the mesiodistal direction.

8. The orthodontic bracket according to claim 1, wherein said bracket body has at least one or at least one pair of projection(s) provided on a side surface of said tie wing where an edge portion of said locking member slides, said projection being capable of abutting against said edge portion, said projection being arranged to be located on an outer side of said edge portion when said slot is closed by said locking member.

9. The orthodontic bracket according to claim 1, wherein said bracket body is provided with a hook rising and jetting out in the mesiodistal direction of the tie wing of said bracket body.

10. The orthodontic bracket according to claim 1, wherein said locking member is formed of a single plate material, and is structured such that a portion of said base side portion located close to said base with a substantially longitudinally central portion as a boundary is set at an angle of inclination conforming to the angulation of said bracket, while said counter base side portion on an opposite side away from the side close to said base is set at an angle of inclination which is obtained by correcting an angle corresponding to a bent portion for pressing said arch wire in addition to the angle of inclination of the bracket angulation, a curved portion connecting said base side portion and said counter base side portion forming a portion of a sine curve.

11. The orthodontic bracket according to claim 1, wherein said bracket body has a rhomboid-type shape, and wherein mesial and distal edge portions of said counter base side portion of said locking member and mesial and distal edge portions of said base side portion, in a top view of said bracket, are formed in parallel along mesial and distal ends of said tie wing of said bracket, and edge portions of said counter base portion extending along the mesiodistal direction are formed to be parallel to said arch wire slot.

12. The orthodontic bracket according to claim 1, wherein said bracket body is of a cut-angulation type in which said arch wire slot is inclined with respect to a tooth axis, and edge portions of said counter base side portion of said locking member extending in the mesiodistal direction are formed to be parallel to said arch wire slot.

13. The orthodontic bracket according to claim 1, wherein said locking member is formed of a superelastic member.

14. The orthodontic bracket according to claim 1, wherein said locking member is formed of a beta titanium alloy.

15. The orthodontic bracket according to claim 1, wherein said locking member is formed of a cobalt-nickel-base alloy (Co—Ni-base alloy) containing chromium (Cr) and molybdenum (Mo).

16. The orthodontic bracket according to claim 1, wherein said locking member is formed of a work-hardening nickel-titanium (Ni—Ti) alloy.

17. The orthodontic bracket according to claim 1, wherein said bracket body has a torque-in-base structure, and said base side portion of said locking member is formed so as to be located in parallel to said base inclined in correspondence with torque.

18. The orthodontic bracket according to claim 17, wherein said base side portion of said locking member is arranged to slide over said base.

19. The orthodontic bracket according to claim 1, wherein said orthodontic bracket is used for first molars of upper and lower jaws, and when the lock member is closed, the lock member covers an upper portion of the arch wire slot in place of a convertible cap to thereby be a tube-shape.

20. The orthodontic bracket according to claim 1, wherein said orthodontic bracket is used for first and second molars of upper and lower jaws, and a distal end of an arch wire is bent before fitting as well as the arch wire can be pulled off without straightening.

* * * * *